United States Patent [19]
Shida et al.

[11] Patent Number: 5,763,619
[45] Date of Patent: Jun. 9, 1998

[54] PROCESS FOR THE PRODUCTION OF TETRAZOLYL COMPOUNDS

[75] Inventors: Yasushi Shida; Kokichi Yoshida, both of Osaka, Japan

[73] Assignee: Takeda Chemical Industries, Ltd., Osaka, Japan

[21] Appl. No.: 697,010

[22] Filed: Aug. 16, 1996

Related U.S. Application Data

[62] Division of Ser. No. 378,825, Jan. 27, 1995, Pat. No. 5,578,733.

[30] Foreign Application Priority Data

Jan. 28, 1994 [JP] Japan .................. 6-008233

[51] Int. Cl.$^6$ .................. C07D 257/06; C07D 487/02; C07D 221/04
[52] U.S. Cl. .................. 548/251; 548/252; 548/253; 544/236; 546/112
[58] Field of Search .................. 548/251, 252, 548/253

[56] References Cited

U.S. PATENT DOCUMENTS 5,196,444  3/1993  Naka et al. .................. 514/381
5,371,233  12/1994  Daumas et al. .................. 548/250

FOREIGN PATENT DOCUMENTS

| | | |
|---|---|---|
| 0 291 969 | 11/1988 | European Pat. Off. . |
| 459 136 | 12/1991 | European Pat. Off. . |
| 0 470 794 | 2/1992 | European Pat. Off. . |
| 0 531 874 | 2/1992 | European Pat. Off. . |
| 93/04059 | 3/1993 | European Pat. Off. . |
| 0 539 713 | 5/1993 | European Pat. Off. . |
| 0 550 313 | 7/1993 | European Pat. Off. . |
| 42 12 748 | 10/1993 | Germany . |

OTHER PUBLICATIONS

Protoghese, "Discovery of a Novel Class of Orally Active, Non-Peptide Angiotensin II Antagonists", Journal of Medical Chemistry, (1992).

*Primary Examiner*—Johann Richter
*Assistant Examiner*—Ebenezer Sackey
*Attorney, Agent, or Firm*—Foley & Lardner

[57] ABSTRACT

Disclosed is a method for removing a protective group of an N-protected tetrazolyl compound which comprises reacting said N-protected tetrazolyl compound with a mineral acid under substantially anhydrous conditions in the presence of an alcohol, insuring a high reaction yield of the object tetrazolyl compound.

11 Claims, No Drawings

PROCESS FOR THE PRODUCTION OF TETRAZOLYL COMPOUNDS

This application is a division of application Ser. No. 08/378,825 filed Jan. 27, 1995 now U.S. Pat. No. 5,578,733.

FIELD OF THE INVENTION

This invention relates to a technology for producing tetrazolyl compounds.

SUMMARY OF THE INVENTION

The present inventors explored in earnest for an industrially useful technology for deprotecting N-protected tetrazolyl compounds and discovered that the object tetrazolyl compound of high purity can be easily obtained by reacting the starting N-protected tetrazolyl compound with a mineral acid under substantially anhydrous conditions in the presence of an alcohol. This invention has been developed on the basis of the above finding.

This invention, therefore, relates to (1) a process for removing a protective group of an N-protected tetrazolyl compound which comprises reacting said N-protected tetrazolyl compound with a mineral acid under substantially anhydrous conditions in the presence of an alcohol, (2) a process for removing a protective group of an N-protected tetrazolyl compound which comprises reacting said N-protected tetrazolyl compound with hydrogen halide in the presence of an alcohol, (3) a process for producing a tetrazolyl compound which comprises reacting an N-protected tetrazolyl compound with a mineral acid under substantially anhydrous conditions in the presence of an alcohol, and (4) a process for producing a tetrazolyl compound which comprises reacting an N-protected tetrazolyl compound with hydrogen halide in the presence of an alcohol.

The compounds produced in accordance with the process of the invention are useful as therapeutics for not only hypertension but also circulatory diseases such as heart failure, strokes, cerebral apoplexy, nephropathy and nephritis. They may be used in the same manner as the products produced in U.S. Pat. No. 5,196,444, EP 459136, and so on, which are incorporated herein by reference.

DETAILED DESCRIPTION OF THE INVENTION

The object of this invention is to deprotect an N-protected tetrazolyl compound to provide the corresponding tetrazolyl compound. For example, this invention comprises subjecting an N-protected tetrazolyl compound to solvolysis by dissolving an N-protected tetrazolyl compound in an inert solvent and either adding an alcohol and introducing a mineral acid under substantially anhydrous conditions or adding an alcohol containing a mineral acid under substantially anhydrous conditions, to provide the corresponding tetrazolyl compound and an ether obtained by reacting the protective group of the N-protected tetrazolyl compound with the alcohol. The reaction product mixture is subjected, where necessary, to extraction, washing, concentration, etc., and an aliphatic hydrocarbon solvent is then added, whereupon the desired tetrazolyl compound is crystallized with high efficiency and in good yield, because the ether in the reaction mixture is extremely highly lipophilic compared to the tetrazolyl compound and is dissolved in the aliphatic hydrocarbon solvent.

In accordance with this invention, the object tetrazolyl compound can be obtained in good yield even when the starting N-protected tetrazolyl compound contains a moiety liable to be cleaved by acid hydrolysis, such as an esterified carboxyl group and an alkoxy group.

Therefore, although the N-protected tetrazolyl compound that can be used in this invention is virtually not limited, the invention is particularly useful when the starting N-protected tetrazolyl compound has at least one hydrolizable group other than the protective group of the N-protected tetrazolyl compound. For example, the N-protected tetrazolyl compound includes a compound of the following general formula (I)

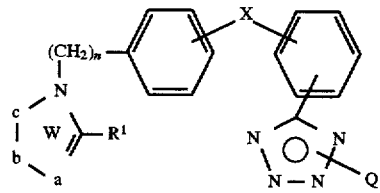

wherein ring W is a nitrogen-containing heterocyclic residue which may be substituted; $R^1$ is a hydrogen atom or a hydrocarbon residue which may be bonding through a hetero atom and/or be substituted; X means that the phenylene group and phenyl group are coupled either directly or through a spacer group comprising a linkage of not more than 2 atoms, n represents 1 or 2, a and b constituting the heterocyclic ring independently represent one or two carbon or hetero atoms which may be substituted; c represents a carbon or hetero atom which may be substituted; Q is a protective group.

The hydrocarbon residue $R^1$ includes alkyl, alkenyl, alkinyl, cycloalkyl, aryl and aralkyl groups, among others, and is preferably alkyl, alkenyl or cycloalkyl. This hydrocarbon residue may be attached to ring W through a hetero atom.

The alkyl group for $R^1$ is a lower alkyl group of 1 to about 8 carbon atoms, which may be straight-chain or branched, thus typically including methyl, ethyl, propyl, isopropyl, butyl, isobutyl, sec-butyl, t-butyl, pentyl, i-pentyl, hexyl, heptyl and octyl.

The alkenyl group for $R^1$ is a lower alkenyl group of 2 to about 8 carbon atoms, which may be straight-chain propenyl, 2-butenyl, 3-butenyl, isobutenyl and 2-octenyl.

The alkinyl group for $R^1$ is a lower alkinyl group of 2 to about 8 carbon atoms, which may be straight-chain or branched, thus typically including ethinyl, 2-propinyl, 2-butinyl, 2-pentinyl and 2-octinyl.

The cycloalkyl group for $R^1$ is a lower cycloalkyl group of 3 to about 6 carbon atoms, thus typically including cyclopropyl, cyclobutyl, cyclopentyl and cyclohexyl.

The above-mentioned alkyl, alkenyl, alkinyl and cycloalkyl groups may respectively be substituted by, for example, hydroxy, amino which may be substituted (e.g. amino, N-lower($C_{1-4}$)alkylamino, N,N-di-lower($C_{1-4}$)alkylamino, etc.), halogen, lower($C_{1-4}$)alkoxy and/or lower ($C_{1-4}$)alkylthio.

The aralkyl group for $R^1$ includes phenyl-lower($C_{1-4}$)alkyl groups such as benzyl, phenethyl and so on. The aryl group for $R^1$ may for example be phenyl.

The above-mentioned aralkyl and aryl groups may respectively be substituted, in any substitutable position or positions of the benzene ring, by, for example, halogen (e.g. F, Cl, Br, etc.), nitro, amino which may be substituted (e.g. amino, N-lower($C_{1-4}$)alkylamino, N,N-di-lower($C_{1-4}$)

alkylamino, etc.), lower($C_{1-4}$)alkoxy (e.g. methoxy, ethoxy, etc.), lower($C_{1-4}$)alkylthio (e.g. methylthio, ethylthio, etc.) and/or lower($C_{1-4}$)alkyl (e.g. methyl, ethyl, etc.).

Among the above-mentioned groups for $R^1$, preferred are alkyl, alkenyl and cycloalkyl groups which may be substituted (e.g. lower($C_{1-5}$)alkyl, lower($C_{2-5}$)alkenyl and lower ($C_{3-6}$)cycloalkyl groups which may be substituted by hydroxy, amino, halogen or lower($C_{1-4}$)alkoxy).

$R^1$ may be bonding through a hetero atom {e.g. nitrogen [N($R^9$)] ($R^9$ means hydrogen or lower($C_{1-4}$)alkyl)]; oxygen or sulfur [—S(O)m— (m is a whole number of 0–2)]}. Particularly preferred is a substituted or unsubstituted alkyl or alkenyl group bonding through a hetero atom (e.g. methylamino, ethylamino, propylamino, propenylamino, isopropylamino, allylamino, butylamino, isobutylamino, dimethylamino, methylethylamino, methoxy, ethoxy, propoxy, isopropoxy, propenyloxy, allyloxy, butoxy, isobutoxy, sec-butoxy, tert-butoxy, 2-butenyloxy, 3-butenyloxy, isobutenyloxy, pentoxy, isopentoxy, hexyloxy, methylthio, ethylthio, propylthio, isopropylthio, allylthio, butylthio, -isobutylthio, sec-butylthio, tert-butylthio, 2-butenylthio, 3-butenylthio, isobutenylthio, pentylthio, isopentylthio, hexylthio, etc.)

X means that the mutually adjacent phenylene and phenyl groups are coupled either directly or through a spacer group comprising a linkage of not more than 2 atoms (preferably coupled directly). The spacer group comprising a linkage of not more than 2 atoms can be any divalent group whose number of atoms constituting the linear spacing moiety is 1 or 2 and which may optionally have a side chain. Thus, for example, lower($C_{1-4}$)alkylene, —CO—, —O—, —S—, —NH—, —CO—NH—, —O—CH$_2$—, —S—CH$_2$— and —CH=CH—, among others, can be mentioned. n represents 1 or 2 (preferably 1).

Referring to the moiety relevant to said X and n, which can be represented by the formula

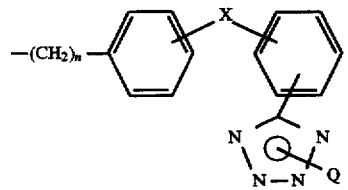

structures of the following formula are preferred.

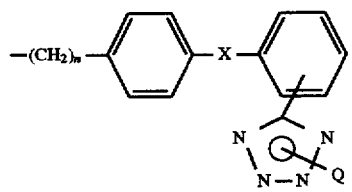

The above-mentioned nitrogen-containing heterocyclic residue, designated by ring W, typically includes the following residues.

In the formulas presented below, $R^1$ is as defined hereinbefore.

Thus, for example, groups which can be represented by the following general formula (II) can be mentioned.

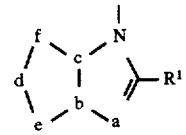

wherein, among the ring-constituent members of the heterocyclic residue, a and e independently represent one or two carbon or hetero atoms which may be substituted, d and f independently represent a carbon or hetero atom which may be substituted, and b and c independently represent a carbon or nitrogen atom which may be substituted.

The following is a partial list of compounds (II):

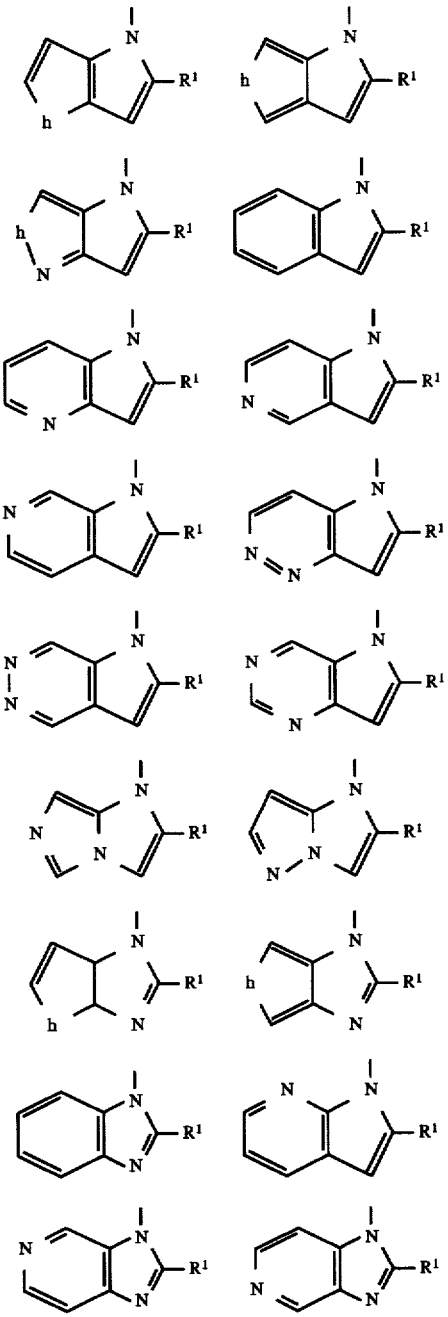

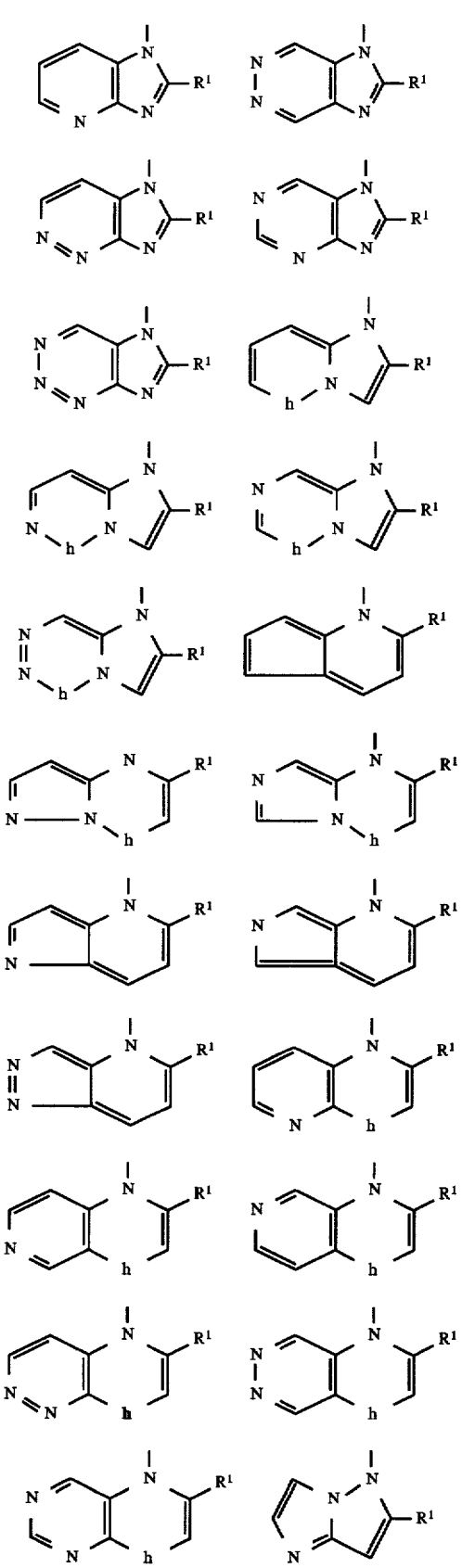
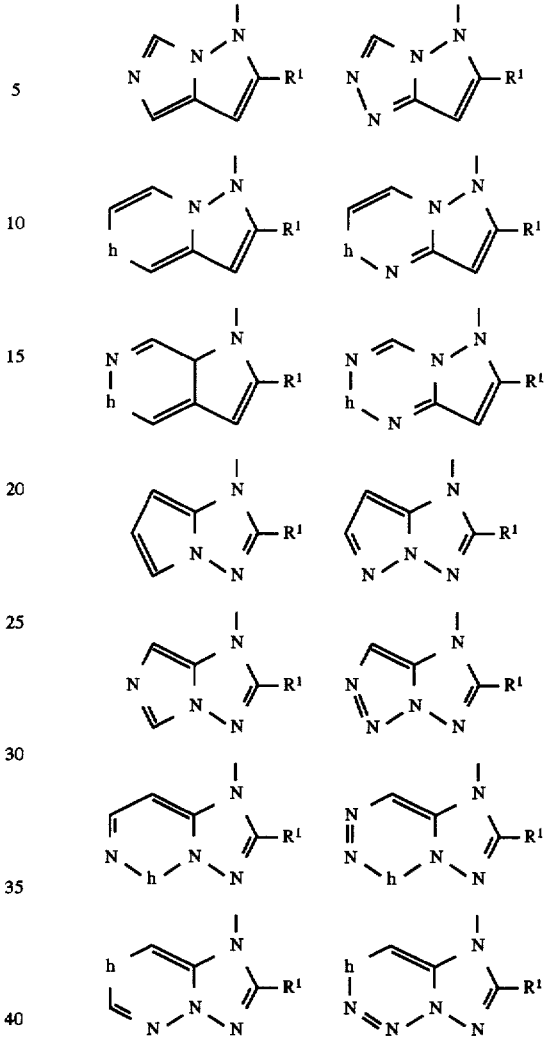

(In the above formulas, h represents —CH$_2$—, >C=), >C=S, >S—(O)m, —N(R$^9$)— or —O—; m and R$^9$ are as defined hereinbefore)

Further examples of said nitrogen-containing heterocyclic residue are represented by the following formula (III).

wherein, among the ring-constituent members of the heterocyclic residue, a and b independently represent one or two carbon or hetero atoms which may be substituted; c represents one carbon or hetero atom which may be substituted. The following is a partial list of compounds (III).

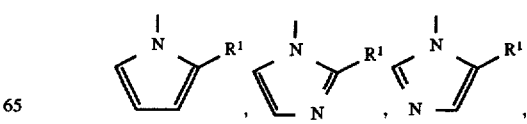

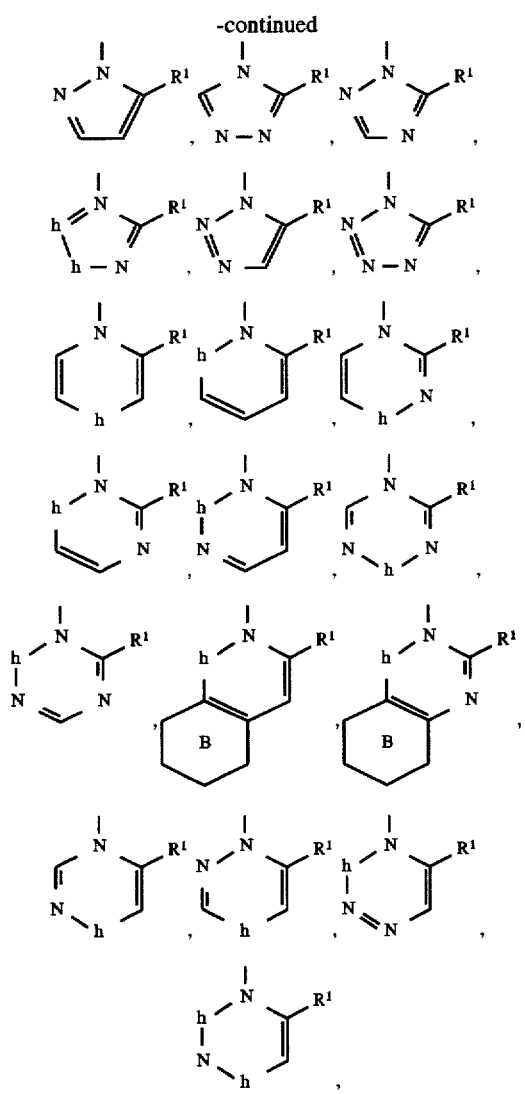

wherein B represents an aromatic hydrocarbon or heterocyclic residue (preferably an aromatic hydrocarbon residue such as phenyl) which may be substituted and may contain one or more hetero atoms; h and h' each represents —CH$_2$—, >C=O, >C=S, >S—(O)m, —N(R$^9$)— or —O—; m and R$^9$ are as defined hereinbefore.

The heterocyclic residue of the above formula (II) may be substituted by a group shown as R$^2$ (for example an anion-forming group or a group convertible thereto), in addition to the substituent group designated by R$^1$. The preferred position of R$^2$ is on the atom designated by f in the formula (II).

As examples of R$^2$ which is a group which releases a proton or is convertible thereto in vivo, carboxyl which may be esterified, tetrazolyl, phosphoric acid residue, sulfonic acid residue, etc. can be mentioned. These groups may be protected by lower alkyl which may be substituted or acyl. Thus, R$^2$ may be any group capable of releasing a proton or being convertible to such a group under biological or physiological conditions (for example through e.g. oxidation, reduction or hydrolysis catalyzed by a physiological enzyme).

The carboxyl which may be esterified, mentioned above for R, includes —COOH, salts thereof, —COOMe, —COOEt, —COOtBu, —COOPr, pivaloyloxymethoxycarbonyl,
1-(cyclohexyloxycarbonyloxy)ethoxycarbonyl, 5-methyl-2-oxo-1,3-dioxolen-4-ylmethoxycarbonyl, acetoxymethyloxy-carbonyl, propionyloxymethoxycarbonyl, n-butyryloxymethoxycarbonyl, isobutyryloxymethoxycarbonyl, 1-(ethoxycarbonyloxy)ethoxycarbonyl, 1-(acetyloxy)ethoxy-carbonyl, 1-(isobutyryloxy)ethoxycarbonyl, cyclohexyl-carbonyloxymethoxycarbonyl, benzoyloxymethoxycarbonyl, cinnamyloxycarbonyl, cyclopentyl-carbonyloxymethoxycarbonyl and so on.

The heterocyclic residue of formula (II) may be further substituted, in addition to the substituent groups designated by R$^1$ and R$^2$, respectively. The substituent that may be additionally present includes halogen (e.g. F, Cl, Br, etc.), cyano, nitro, lower(C$_{1-4}$)alkyl, lower(C$_{1-4}$) alkoxy, amino which may be substituted [e.g. amino, N-lower(C$_{1-4}$) alkylamino (e.g. methylamino etc.), N,N-di-lower(C$_{1-4}$) alkylamino (e.g. dimethylamino etc.), N-arylamino (e.g. phenylamino etc.) and cyclic amino (e.g. morpholino, piperidino, piperazino, N-phenylpiperazino, etc.)], groups of the formula —CO—D' [wherein D' represents a hydroxyl group or a lower(C$_{1-4}$)alkoxy group, the alkyl moiety of which may be substituted by hydroxy, lower(C$_{1-4}$)alkoxy, lower(C$_{2-6}$)alkanoyloxy (e.g. acetoxy, pivaloyloxy, etc.) or lower(C$_{1-6}$)alkoxycarbonyloxy (e.g. methoxy-carbonyloxy, ethoxycarbonyloxy, cyclohexyloxycarbonyloxy, etc.)], tetrazoyl which may be protected by lower(C$_{1-4}$)alkyl or acyl (e.g. lower(C$_{2-5}$)alkanoyl, benzoyl which may be substituted, etc.), phosphoric acid residue or sulfonic acid residue. Preferred substituent groups are lower(C$_{1-4}$)alkyl and halogen. One or two such substituents may be present in any substitutable position or positions of the heterocycle.

The fused heterocyclic residue of formula (II) preferably has one of the following structures:

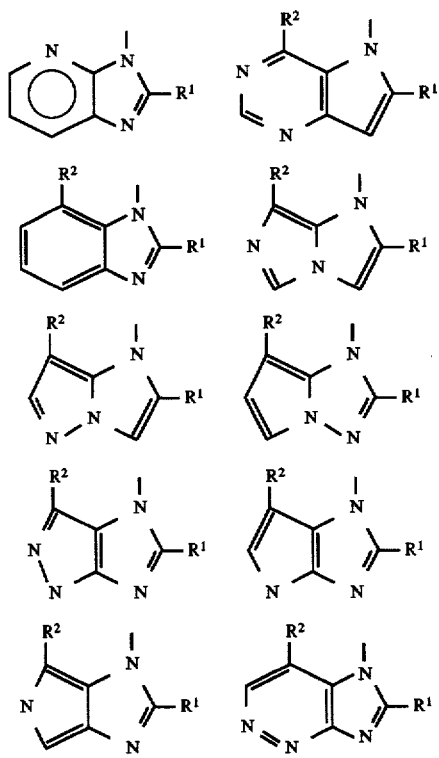

-continued

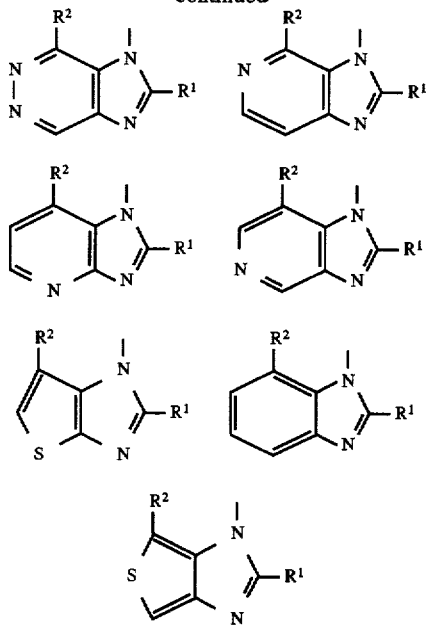

(wherein R¹ and R² are as defined hereinbefore). Particularly preferred are heterocyclic residues having a benzimidazole, thieimidazole or imidazopyridine nucleus. The most desirable nuclei are benzimidazole and thieimidazole.

The heterocyclic residue of general formula (III) may have further substituents in addition to the substituent group designated by $R^1$. Among such substituents are halogen (e.g. F, Cl, Br, etc.), cyano, nitro, lower($C_{1-4}$)alkyl that may be substituted, lower($C_{1-4}$)alkoxy, amino which may be substituted [e.g. amino, N-lower($C_{1-4}$)alkylamino (e.g. methylamino etc.), N,N-di-lower($C_{1-4}$)alkylamino (e.g. dimethylamino etc.), N-acrylamino (e.g. 2-methylacryloylamino etc.), N-arylamino (e.g. phenylamino etc.), and cyclic amino (e.g. morpholino, piperidino, piperazino, N-phenylpiperazino, etc.)], groups of the formula —CO—D' [wherein D' represents a hydroxyl group or a lower($C_{1-4}$)alkoxy group, the alkyl moiety of which may be substituted by hydroxy, lower($C_{1-4}$)alkoxy, lower($C_{2-6}$) alkanoyloxy (e.g. acetoxy, pivaloyloxy, etc.) or lower($C_{1-6}$) alkoxycarbonyloxy (e.g. methoxycarbonyloxy, ethoxycarbonyloxy, cyclohexyloxycarbonyloxy, etc.)], tetrazoyl which may be protected by lower($C_{1-4}$)alkyl or acyl (e.g. lower($C_{2-5}$)alkanoyl, benzoyl which may be substituted, etc.), trifluoromethanesulfonamide, phosphoric acid residue or sulfonic acid residue. Preferred substituent groups are lower($C_{1-4}$)alkyl which may be substituted and halogen. One or two such substituents may occur in the substitutable position or positions of the heterocycle. The substituent for said lower($C_{1-4}$)alkyl that may be substituted may for example be hydroxy, carboxy or halogen.

Among compounds of formula (I), those compounds which can be represented by the following formula (I') are preferred.

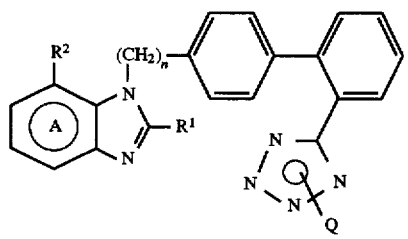

wherein ring A represents a benzene ring which may have further substituents in addition to the group designated by $R^2$, $R^1$ represents hydrogen or lower ($C_{1-6}$), preferably ($C_{1-4}$), alkyl which may be attached through a hetero atom (e.g. O, N (H), S) and/or substituted; $R^2$ represents a carboxyl group which may be esterified; Q' represents triphenylmethyl; n is equal to 1 or 2.

Referring to the above formula (I'), the substituent group of $R^1$ may for example be hydroxy, amino, halogen or lower($C_{1-4}$)alkoxy.

Referring, further, to formula (I'), the substituent group or groups other than the group $R^2$ on ring A may be halogen (e.g. F, Cl, Br, etc.), lower($C_{1-4}$)alkyl, lower($C_{1-4}$)alkoxy, nitro, groups of the formula —CO—D' [wherein D' represents a hydroxyl group or a lower($C_{1-4}$)alkoxy group, the alkyl moiety of which may be substituted by hydroxy, lower($C_{1-4}$)alkoxy, lower($C_{2-6}$) alkanoyloxy (e.g. acetoxy, pivaloyloxy, etc.) or lower($C_{1-6}$) alkoxycarbonyloxy (e.g. methoxycarbonyloxy, ethoxycarbonyloxy, cyclohexyloxycarbonyloxy, etc.)] and amino which may be substituted by ($C_{1-4}$)alkyl (preferably, lower($C_{1-4}$)alkyl), halogen, etc). As for ring A, a benzene ring not substituted except by the group $R^2$ is still more preferred.

The compound of general formula (I) can be produced in accordance with the disclosure in JP Kokai H4-364171/1992, EP459136, EP425921, for instance.

The protective group of the N-protected tetrazolyl compound in the context of this invention includes an optionally substituted multiphenylmethyl group (e.g. triphenylmethyl, 4-methoxytriphenylmethyl, 4,4'-dimethoxytriphenylmethyl, 4,4',4"-trimethoxytriphenylmethyl, 4,4'-dimethoxydiphenylmethyl, etc.) and o-nitrobenzenesulfenyl, and is preferably triphenylmethyl or 4,4'-dimethoxydiphenylmethyl.

The alcohol which can be employed in this invention includes methanol, ethanol, 1-propanol, 2-propanol, 1-butanol, 2-methyl-1-propanol, 2-butanol, 2-methyl-2-propanol, 1-pentanol, 2-pentanol, 3-pentanol, 2-methyl-1-butanol, 3-methyl-2-butanol, etc. and is preferably a lower ($C_{1-4}$)alcohol such as methanol, ethanol, 1-propanol, 2-propanol, 1-butanol, 2-methyl-1-propanol, 2-butanol, 2-methyl-2-propanol, etc.

The mineral acid which can be employed in this invention can be any acid that is under substantially anhydrous conditions. The term "substantially anhydrous conditions" means conditions in which water does not substantially take part in the reaction. For example, hydrogen halide, concentrated sulfuric acid, can be mentioned. Particularly preferred are hydrogen halide.

For example, the concentration of water is at most 1 mol, preferably at most 0.5 mol, per mole of the N-protected tetrazolyl compound.

The hydrogen halide which can be employed in this invention includes hydrogen fluoride, hydrogen chloride, hydrogen bromide, hydrogen iodide, etc. and is preferably hydrogen chloride.

The concentration of the concentrated sulfuric acid is at least 95%, preferably 98%.

This invention is, for example, carried into practice by dissolving said N-protected tetrazolyl compound in an inert solvent and either adding an alcohol and introducing a mineral acid under substantially anhydrous conditions or adding an alcohol containing a mineral acid under substantially anhydrous conditions.

The amount of the alcohol to be added is not so critical but is at least one mole, generally 2–100 moles, preferably 5–50 moles, per mole of the N-protected tetrazolyl compound.

The inert solvent for the N-protected tetrazolyl compound can be any solvent that does not take part in the reaction and is capable of dissolving the N-protected tetrazolyl compound. For example, methylene chloride, ethyl acetate, toluene, dioxane, tetrahydrofuran, xylene, chloroform and carbon tetrachloride can be mentioned. Particularly preferred are methylene chloride, ethyl acetate and toluene. These solvents can be used singly or in a suitable combination of 2 or more species. As to this solvent, the alcohol for use in said introduction or dissolution of hydrogen chloride can be utilized as the reaction solvent as well.

The amount of the solvent to be used is not so critical but is generally 2–10 or preferably 3–5 volumes relative to the N-protected tetrazolyl compound.

The amount of mineral acid is not so critical, either, but is generally 1–5 equivalents or preferably 1–2 equivalents relative to the N-protected tetrazolyl compound.

The reaction temperature is not critical but is generally −5–30° C. and preferably not higher than 10° C. The reaction time, which is not particularly restricted, is generally 1–6 hours and preferably 1–3 hours.

The reaction product mixture is subjected, where necessary, to extraction, washing, concentration, etc., and an aliphatic hydrocarbon solvent is then added, whereupon the desired tetrazolyl compound is crystallized.

The aliphatic hydrocarbon solvent that can be used includes pentane, hexane, heptane and others but is preferably hexane or heptane. This aliphatic hydrocarbon solvent can be used in admixture with an inert solvent. The inert solvent that can be used includes lower($C_{1-4}$) alcohols (e.g. methanol, ethanol, propanol, butanol, etc.), acetone, methylene chloride, ethyl acetate, toluene, acetonitrile and so on. Particularly preferred is acetone.

In accordance with this invention, the objective tetrazolyl compound can be obtained as crystals of high quality in good yield.

The compounds produced in accordance with the process of the invention are specifically disclosed as follows:

(±)-1-(cyclohexyloxycarbonyloxy)ethyl 2-ethoxy-1-[[2'-(1H-tetrazol-5-yl)biphenyl-4-yl]methyl]-1H-benzimidazole-7-carboxylate, 2-ethoxy-1-[[2'(1H-tetrazol-5-yl)biphenyl-4-yl]methyl]-1H-benzimidazole-7-carboxylic acid, Ethyl 2-ethoxy-1-[[2'-(1H-tetrazol-5-yl)biphenyl-4-yl]methyl]benzimidazole-7-carboxylate, Methyl 2-ethoxy-1-[[2'-(1H-tetrazol-5-yl)biphenyl-4-yl]methyl]benzimidazole-7-carboxylate, Methyl 2-methoxy-1-[[2'-(1H-tetrazol-5-yl)biphenyl-4-yl]methyl]benzimidazole-7-carboxylate, 2-Methoxy-1-[[2'-(1H-tetrazol-5-yl)biphenyl-4-yl]methyl]benzimidazole-7-carboxylic acid, Pivaloyloxymethyl 2-butyl-1-[[2'-(1H-tetrazol-5-yl)biphenyl-4-yl]methyl]-1H-benzimidazole-7-carboxylate, Pivaloyloxymethyl 2-ethoxy-1-[[2'-(1H-tetrazol-5-yl)biphenyl-4-yl]methyl]benzimidazole-7-carboxylate, Ethyl 2-propoxy-1-[[2'-(1H-tetrazol-5-yl)biphenyl-4-yl]methyl]benzimidazole-7-carboxylate, 2-Propoxy-1-[[2'-(1H-tetrazol-5-yl)biphenyl-4-yl]methyl]benzimidazole-7-carboxylic acid, (5-Methyl-2-oxo-1,3-dioxolen-4-yl)methyl 2-ethoxy-1-[[2'-(1H-tetrazol-5-yl)biphenyl-4-yl]methyl]benzimidazole-7-carboxylate, Acetoxymethyl 2-ethoxy-1-[[2'-(1H-tetrazol-5-yl)biphenyl-4-yl]methyl]benzimidazole-7-carboxylate, Propionyloxymethyl 2-ethoxy-1-[[2'-(1H-tetrazol-5-yl)biphenyl-4-yl]methyl]benzimidazole-7-carboxylate, Butyryloxymethyl 2-ethoxy-1-[[2'-(1H-tetrazol-5-yl)biphenyl-4-yl]methyl]benzimidazole-7-carboxylate, Isobutyryloxymethyl 2-ethoxy-1-[[2'-(1H-tetrazol-5-yl)biphenyl-4-yl]methyl]benzimidazole-7-carboxylate, 1-(Ethoxycarbonyloxy)ethyl 2-ethoxy-1-[[2'-(1H-tetrazol-5-yl)biphenyl-4-yl]methyl]benzimidazole-7-carboxylate, 1-Acetoxyethyl 2-ethoxy-1-[[2'-(1H-tetrazol-5-yl)biphenyl-4-yl]methyl]benzimidazole-7-carboxylate, 1-(Isopropoxycarbonyloxy)ethyl 2-ethoxy-1-[[2'-(1H-tetrazol-5-yl)biphenyl-4-yl]methyl]benzimidazole-7-carboxylate, Cyclohexylcarbonyloxymethyl 2-ethoxy-1-[[2'-(1H-tetrazol-5-yl)biphenyl-4-yl]methyl]benzimidazole-7-carboxylate, Benzoyloxymethyl 2-ethoxy-1-[[2'-(1H-tetrazol-5-yl)biphenyl-4-yl]methyl]benzimidazole-7-carboxylate, (E)-Cinnamoyloxymethyl 2-ethoxy-1-[[2'-(1H-tetrazol-5-yl)biphenyl-4-yl]methyl]benzimidazole-7-carboxylate, Cyclopentylcarbonyloxymethyl 2-ethoxy-1-[[2'-(1H-tetrazol-5-yl)biphenyl-4-yl]methyl]benzimidazole-7-carboxylate, Pivaloyloxymethyl 2-ethylamino-1-[[2'-(1H-tetrazol-5-yl)biphenyl-4-yl]methyl]benzimidazole-7-carboxylate, 1-(Cyclohexyloxycarbonyloxy)ethyl 2-ethylamino-1-[[2'-(1H-tetrazol-5-yl)biphenyl-4-yl]methyl]benzimidazole-7-carboxylate, Methyl 2-allyloxy-1-[[2'-(1H-tetrazol-5-yl)biphenyl-4-yl]methyl]benzimidazole-7-carboxylate, Methyl 2-butoxy-1-[[2'-(1H-tetrazol-5-yl)biphenyl-4-yl]methyl]benzimidazole-7-carboxylate, In accordance with this invention, as contrasted to the processes involving the presence of water in the reaction system, the decomposition reaction is remarkably inhibited even when the starting N-protected tetrazolyl compound has a partial structure liable to undergo hydrolysis under acidic conditions, thus insuring a high reaction yield of the objective tetrazolyl compound.

Since a tetrazolyl compound can be produced with high efficiency and in good yield by deprotecting the N-protected tetrazolyl compound in accordance with this invention, a commercially useful production technology is provided for tetrazolyl compounds.

The following examples are intended to describe this invention in further detail and should by no means be construed as defining the scope of the invention.

EXAMPLE 1

In 29 mL of methylene chloride was dissolved 10.00 g of (±)-1-(cyclohexyloxycarbonyloxy)ethyl 2-ethoxy-1-[2'-(N-triphenylmethyl-1H-tetrazol-5-yl)biphenyl-4-yl] methylbenzimidazole-7-carboxylate followed by addition of 23 mL of methanol and cooling to 5° C. Then, 6 mL of methanol containing 0.53 g of hydrogen chloride as dissolved was added dropwise at 5° C. over a period of 15 minutes. The mixture was further stirred at 5° C. for 3.5 hours, at the end of which time 19 mL of ethyl acetate and 19 mL of water were added. The mixture was adjusted to pH 6.3 with a saturated aqueous solution of sodium hydrogen carbonate and, then, 10 mL of ethyl acetate and 10 mL of 20% NaCl—$H_2O$ were added. The aqueous layer was separated and extracted with 20 mL of ethyl acetate. The ethyl acetate layers were combined and redistributed into 20% NaCl and 38 mL of ethyl acetate. The organic layer was separated and concentrated and the residue was diluted with ethanol and reconcentrated. To the residue was added 20 mL of acetone and the mixture was stirred at room temperature for 3 hours for sufficient crystallization. Thereafter, 90 mL of hexane was added and the mixture was further stirred at room temperature for 1 hour and, then, under ice-cooling for 2 hours. The resulting crystals were collected by filtration and washed with 25 mL of acetone-hexane (1:9). The crystals were dried under reduced pressure to provide 6.90 g of (±)-1-(cyclohexyloxycarbonyloxy)ethyl 2-ethoxy-1-[2'-(1H-tetrazol-5-yl) biphenyl-4-yl]methylbenzimidazole-7-carboxylate (yield 92%).

$^1$H-NMR (200 MHz, $CDCl_3$) δ: 1.2–1.53 (12H, m), 1.69 (2H, m), 1.89 (2H, m), 4.55–4.69 (3H, m), 5.51 (1H, d), 5.61 (1H, d), 6.75–7.01 (11H, m), 7.13–7.46 (13H, m), 7.57 (1H, dd), 7.75 (1H, dd), 7.84–7.89 (1H, m)

IR (KBr) $cm^{-1}$:2942, 1754, 1717, 1615, 1476

EXAMPLE 2

In a mixture of 17 mL of methylene chloride and 13 mL of methanol was dissolved 5.79 g of pivaloyloxymethyl 2-ethoxy-1-[2'-(N-triphenylmethyl-1H-tetrazol-5-yl) biphenyl-4-yl]methylbenzimidazole-7-carboxylate and the solution was cooled to 5° C. To this solution was added 3.7 mL of methanol containing 0.344 g of hydrogen chloride dropwise and the mixture was stirred at 5°–6° C. for 2 hours. Then, 11 mL of ethyl acetate and 11 mL of water were added and the mixture was adjusted to pH 6.2 with a saturated aqueous solution of sodium hydrogen carbonate. Then, 6 mL of ethyl acetate and 20% NaCl—$H_2O$ were added. The aqueous layer was taken and extracted with 12 mL of ethyl acetate. The organic layers were combined and redistributed into 22 mL of ethyl acetate and 20% NaCl solution. The organic layer was separated and concentrated and the residue was stirred in 15 mL of toluene at room temperature for 30 minutes. Then, 100 mL of hexane was added and the mixture was stirred under ice-cooling for 1 hour. The resulting crystals were collected by filtration, washed with 20 mL of toluene-hexane (1:9), and dried to provide 3.65 g of pivaloyloxymethyl 2-ethoxy-1-[2'-(1H-tetrazol-5-yl)-biphenyl-4-yl]methylbenzimidazole-7-carboxylate (yield 91%).

$^1$H-NMR (200 MHz, $CDCl_3$) δ: 1.13 (9H, s), 1.44 (3H, t), 4.37 (2H, q), 5.61 (2H, s), 5.68 (2H, s), 6.80 (2H, d), 6.93 (2H, d), 6.99–7.11 (2H, m), 7.33–7.37 (1H, m), 7.49–7.54 (1H, m), 7.59–7.62 (2H, m), 8.03–8.07 (1H, m)

IR (KBr) $cm^1$:2986, 1755, 1734, 1614, 1554, 1479, 1429 m.p. 145°–146° C.

EXAMPLE 3

Using 10.0 g of (+)-1-(cyclohexyloxycarbonyloxy)-ethyl 2-ethoxy-1-[2'-(N-triphenylmethyl-1H-tetrazol-5-yl) biphenyl-4-yl]methylbenzimidazole-7-carboxylate, the reaction and after-treatment of Example 1 was repeated except that ethanol was used in lieu of methanol. The procedure provided 6.83 g of (±)-1-(cyclohexyloxycarbonyloxy)ethyl 2-ethoxy-1-[2'-(1H-tetrazol-5-yl)biphenyl-4-yl]methylbenzimidazole-7-carboxylate (yield 91%).

In physicochemical properties, this compound was in agreement with the compound obtained in Example 1.

EXAMPLE 4

The procedure of Example 1 was repeated using 200 mg of ethyl 4-[N-(2-methylacryloyl)amino]-2-n-propyl-1-[[2'-(N-triphenylmethyltetrazol-5-yl)biphenyl-4 -yl]methyl] imidazole-5-carboxylate to provide 76 mg of ethyl 4-[N-(2-methylacryloyl)amino]-2-n-propyl-1-[[2'-(tetrazol-5-yl) biphenyl-4-yl]methyl]-1H-imidazole-5-carboxylate (yield 57%).

$^1$H-NMR (200 MHz, $CDCl_3$) δ: 0.91 (3H, t), 1.23 (3H, t), 1.6–1.7 (2H, m), 2.00 (3H, s), 2.73 (2H, t), 4.28 (2H, dd), 5.50 (2H, s), 5.53 (1H, s), 5.90 (1H, s), 6.92 (1H, d), 7.12 (1H, d), 7.36 (1H, d), 7.49 (1H, t), 7.55 (1H, t), 7.91 (1H, d), 9.62 (1H, s), m.p. 134°–136° C.

COMPARISON EXAMPLE 1

In 15 mL of methylene chloride was dissolved 5.44 g of (±)-1-(cyclohexyloxycarbonyloxy)ethyl 2-ethoxy-1-[2'-(N-triphenylmethyl-1H-tetrazol-5-yl)biphenyl-4-yl] methylbenzimidazole-7-carboxylate followed by addition of 54 mL of methanol and 8.2 mL of 1N—HCl, and the mixture was stirred at 25° C. for 2 hours. Then, 19 mL of water and 19 mL of ethyl acetate were added and the mixture was adjusted to pH 3.2 with a saturated aqueous solution of sodium hydrogen carbonate. The mixture was extracted using 19 mL of water and 54 mL of ethyl acetate and the aqueous layer was separated and extracted with 30 mL of ethyl acetate. The organic layers were combined, washed with 40 mL of water and concentrated under reduced pressure to give an oil. This oil was purified by silica gel chromatography (300 mL, methylene chloride-methanol =10:1) to provide 2.92 g of (±)-1-(cyclohexyloxycarbonyloxy)ethyl 2-ethoxy-1-[2'-(1H-tetrazol-5-yl)biphenyl-4-yl]methylbenzimidazole-7-carboxylate (yield 75%).

The physicochemical properties of this compound were in good agreement with those of the compound obtained in Example 1.

COMPARISON EXAMPLE 2

To 2.0 g of pivaloyloxymethyl 2-ethoxy-1-[2'-(N-triphenylmethyl-1H-tetrazol-5-yl)biphenyl-4-yl] methylbenzimidazole-7-carboxylate were added 30 mL of methanol and 6 mL of 1N-hydrochloric acid and the mixture was stirred at room temperature for 30 minutes. The reaction mixture was then concentrated under reduced pressure and extracted using ethyl acetate and water. The organic layer was separated and concentrated under reduced pressure to give an oil. This oil was purified by silica gel chromatography (100 mL, methylene chloride-methanol=10:1) to provide 1.13 g of pivaloyloxymethyl 2-ethoxy-1-[2'-(1H-tetrazol-5-yl)biphenyl-4-yl]methylbenzimidazole-7-carboxylate (yield 80%).

The physicochemical properties of this compound were in good agreement with the compound obtained in Example 2.

COMPARISON EXAMPLE 3

To 250 mg of ethyl ,4-[N-(2-methylacryloyl)amino]-2-n-propyl-1-[[2'-(N-triphenylmethyltetrazol-5-yl)biphenyl-4- yl]methyl]imidazole-5-carboxylate was added 10 mL of 2N—HCl-ethanol (1:1) and the mixture was stirred at an external temperature of 90° C. for 4 hours. The solvent was then distilled off under reduced pressure and the residue was purified by silica gel chromatography (chloroform-methanol=20:1) and recrystallized from acetonitrile to provide 71 mg of ethyl 4-[N-(2-methylacryloyl)amino]-2-n-propyl-1-[[2'-(tetrazol-5-yl)biphenyl-4-yl]methyl]-1H-imidazole-5-carboxylate (yield 42%).

The physicochemical properties of this compound were in agreement with those of the compound obtained in Example 4.

EXAMPLE 5

In a mixture of 1.5 mL of methylene chloride and 1.5 mL of methanol was dissolved 0.50 g of (±)-1-(cyclohexyloxycarbonyloxy)ethyl 2-ethoxy-1-[2'-(N-triphenylmethyl-1H-tetrazol-5-yl)biphenyl-4 -yl]methylbenzimidazole-7-carboxylate and the solution was cooled to 3° C. To this solution was added 0.040 mL of concentrated sulfuric acid (98%) and the mixture was stirred at 3° C. for 3.5 hours. Then, the reaction mixture was analyzed by HPLC. The peak area ratio of precursor material, product and by-product was shown in Table 1 (Run 1).

The results of experiment carried out with the same procedure as described above using hydrogen chloride instead of concentrated sulfuric acid were also shown in Table 1 (Run 2).

COMPARISION EXAMPLE 4

The results of experiment carried out with the same procedure as described in Example 5 using concentrated hydrochloric acid instead of concentrated sulfuric acid were also shown in Table 1 (Run 3).

TABLE 1

| Run No. | Acid | Reaction temperature | Reaction time | Product[a] | By-product[b] | precursor[c] |
|---|---|---|---|---|---|---|
| 1 | 98% H$_2$SO$_4$ 1.3 eq | 3° C. | 3.5 hr. | 93.6% | 3.5% | 2.9% |
| 2 | HCl (gas) 1.1 eq | 3° C. | 2.5 hr. | 97.9% | 1.0% | 1.0% |
| 3 | 35% HCl aq. 1.3 eq | 3° C. | 5.0 hr. | 88.6% | 10.0% | 1.4% |

[a] (±)-1-(cyclohexyloxycarbonyloxy)ethyl 2-ethoxy-1-[2'-(1H-tetrazol-5-yl)biphenyl-4-yl]methylbenzimidazole-7-carboxylate
[b] (±)-1-(cyclohexyloxycarbonyloxy)ethyl 2-oxo-1-[[2'-(1H-tetrazol-5-yl)biphenyl-4-yl]methyl]-2,3-dihydro-1H-benzimidazole-7-carboxylate
[c] (±)-1-(cyclohexyloxycarbonyloxy)ethyl 2-ethoxy-1-[2'-(N-triphenylmethyl-1H-tetrazol-5-yl)biphenyl-4-yl]methylbenzimidazole-7-carboxylate

What is claimed is:

1. A method for producing a tetrazolyl compound which comprises reacting an N-protected tetrazolyl compound, or a salt thereof, represented by the formula (I):

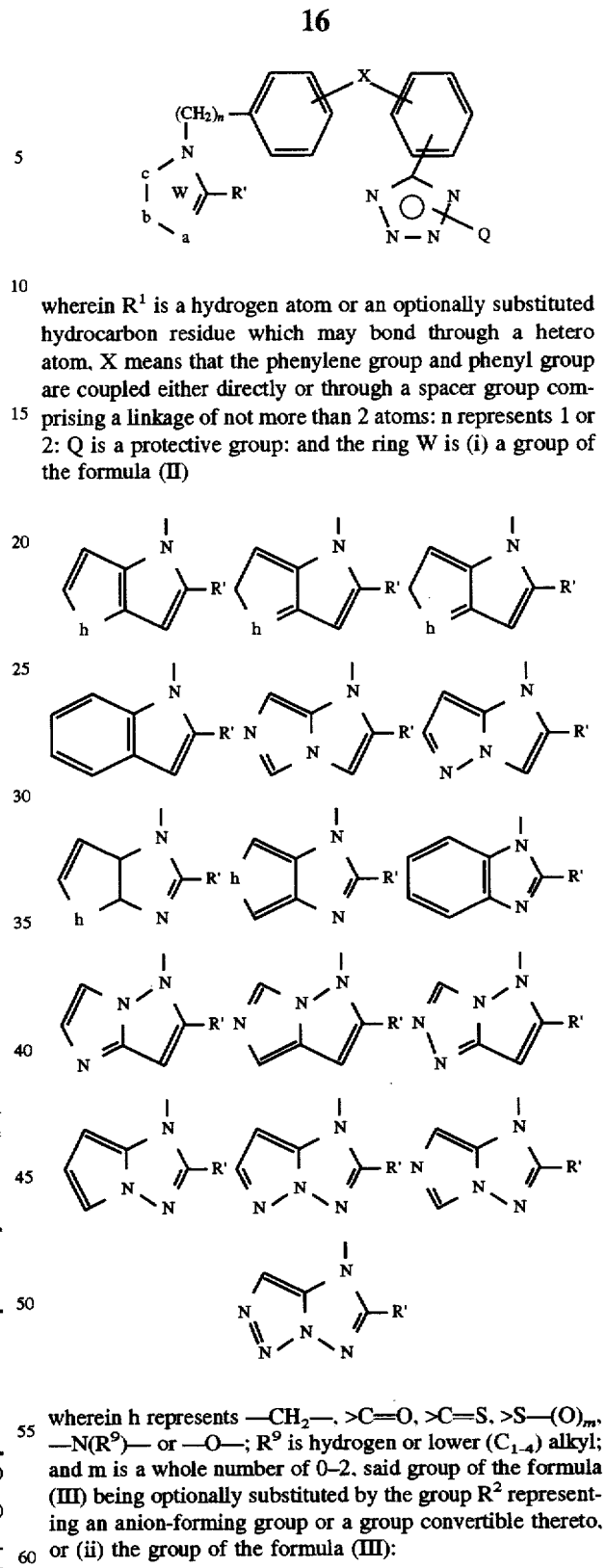

wherein R$^1$ is a hydrogen atom or an optionally substituted hydrocarbon residue which may bond through a hetero atom, X means that the phenylene group and phenyl group are coupled either directly or through a spacer group comprising a linkage of not more than 2 atoms: n represents 1 or 2: Q is a protective group: and the ring W is (i) a group of the formula (II)

wherein h represents —CH$_2$—, >C=O, >C=S, >S—(O)$_m$, —N(R$^9$)— or —O—; R$^9$ is hydrogen or lower (C$_{1-4}$) alkyl; and m is a whole number of 0–2, said group of the formula (III) being optionally substituted by the group R$^2$ representing an anion-forming group or a group convertible thereto, or (ii) the group of the formula (III):

-continued

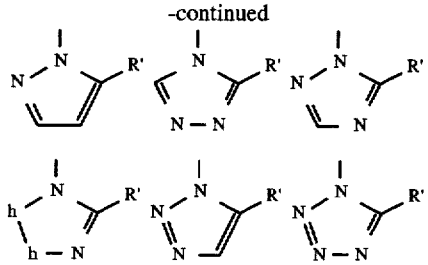

wherein B represents an aromatic hydrocarbon or heterocyclic residue which may be substituted: h and h' each represents —$CH_2$—, >C=O, >C=S, >S—(O)m, —$N(R^9)$— or —O—; m and $R^9$ are as defined hereinbefore, said group of the formula (II) or (III) being optionally substituted by halogen, cyano, nitro, lower ($C_{1-4}$) alkyl, lower ($C_{1-4}$) alkoxy, amino, N-lower ($C_{1-4}$) alkylamino, N,N-di-lower ($C_{1-4}$)alkylamino, N-acrylamino, cyclic amino, a group of the formula —CO—D' wherein D' represents a hydroxyl group or a lower ($C_{1-4}$) alkoxy group, the alkyl moiety of which may be substituted by hydroxy, lower ($C_{1-4}$) alkoxy, lower ($C_{2-6}$) alkanoyloxy, lower ($C_{1-6}$) alkoxycarbonyloxy or cyclohexyloxycarbonyloxy, tetramyl which may be protected by lower ($C_{1-4}$) alkyl or acyl, trifluoromethanesulfonamide, phosphoric acid residue or sulfonic acid residue with a mineral acid under substantially anhydrous conditions in the presence of an alcohol.

2. The method according to claim 1, wherein the mineral acid is hydrogen halide.

3. The method according to claim 2, wherein the hydrogen halide is hydrogen chloride.

4. The method according to claim 1, wherein the mineral acid is concentrated sulfuric acid.

5. The method according to claim 4, wherein the concentration of the concentrated sulfuric acid is at least 95%.

6. The method according to claim 1, wherein Q is an optionally substituted multiphenylmethyl group.

7. The method according to claim 1, wherein Q is triphenylmethyl.

8. The method according to claim 1, wherein Q is 4,4'-dimethoxydiphenylmethyl.

9. The method according to claim 1, wherein said alcohol is a lower ($C_{1-4}$) alcohol.

10. The method according to claim 1, wherein said N-protected tetrazolyl compound has at least one hydrolizable group other than the protective group Q.

11. The method according to claim 1, wherein said N-protected tetrazolyl compound has an esterified carboxyl group or an alkoxy group.

* * * * *

UNITED STATES PATENT AND TRADEMARK OFFICE
CERTIFICATE OF CORRECTION

PATENT NO. : 5,763,619
DATED : June 9, 1998
INVENTOR(S) : Yasushi SHIDA et al.

It is certified that error appears in the above-identified patent and that said Letters Patent is hereby corrected as shown below:

Column 2, line 45, after "straight chain" insert –branched, thus typically including vinyl,--.

Column 6, line 43, delete ">C=)", and insert therefor -->C=0--.

Column 7, line 65, delete "R", and insert therefor --$R^2$,--.

Column 13, line 36, delete "5°-6°C.", and insert therefor --5-6°C--.

Column 13, line 57, delete "145°-146°C.", and insert therefor --145-146°C.--;
line 61, delete "(+)", and insert therefor --(±)--.

Column 14, line 20, delete "134°-136°C.", and insert therefor --134-136°C.--.

Column 16, line 58, delete "(III)" and insert therefor --(II)--.

Column 17, line 24, delete "tetramyl", and insert therefor--tetrazolyl--.

Column 17, lines 12-13, delete, "B represents an aromatic hydrocarbon or heterocyclic residue which may be substituted:".

UNITED STATES PATENT AND TRADEMARK OFFICE
CERTIFICATE OF CORRECTION

PATENT NO. : 5,763,619
DATED : June 9, 1998
INVENTOR(S) : Yasushi SHIDA et al.

It is certified that error appears in the above-identified patent and that said Letters Patent is hereby corrected as shown below:

Column 16, delete:

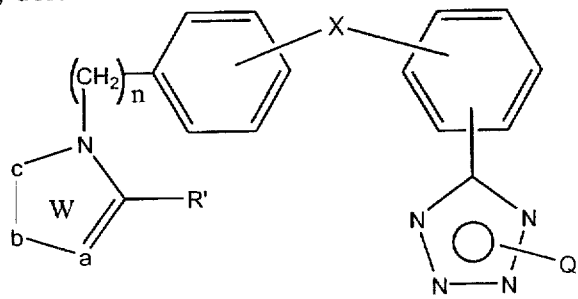

and insert therefor

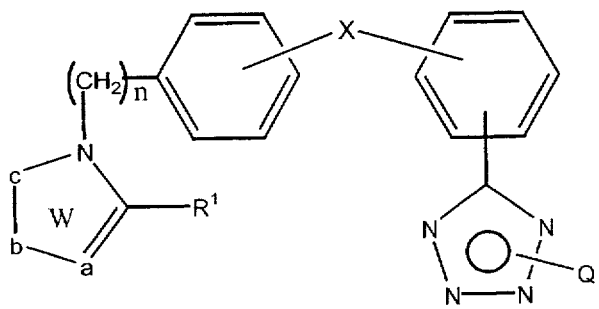

UNITED STATES PATENT AND TRADEMARK OFFICE
CERTIFICATE OF CORRECTION

PATENT NO. : 5,763,619
DATED : June 9, 1998
INVENTOR(S) : Yasushi SHIDA et al.

It is certified that error appears in the above-identified patent and that said Letters Patent is hereby corrected as shown below:

Column 16, lines 20-50, delete:

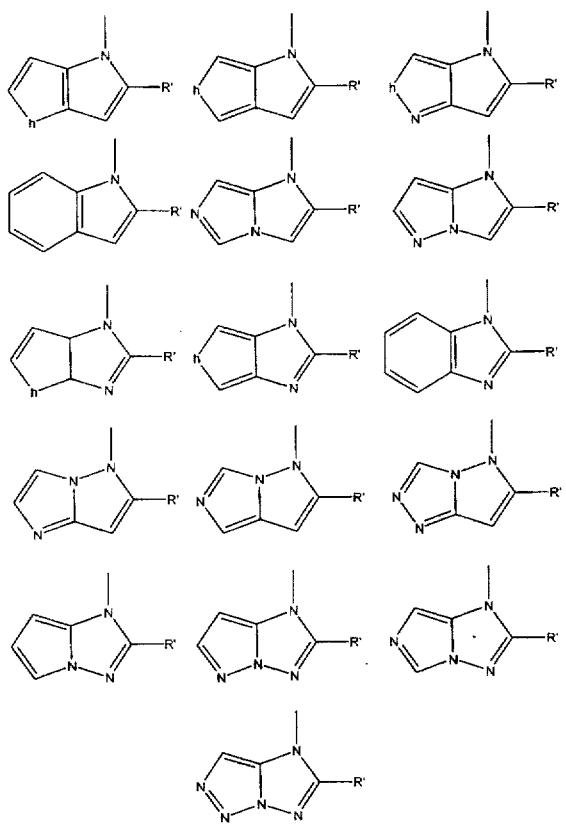

UNITED STATES PATENT AND TRADEMARK OFFICE
CERTIFICATE OF CORRECTION

PATENT NO. : 5,763,619
DATED : June 9, 1998
INVENTOR(S) : Yasushi SHIDA et al.

Page 4 of 7

It is certified that error appears in the above-identified patent and that said Letters Patent is hereby corrected as shown below:

and insert therefore

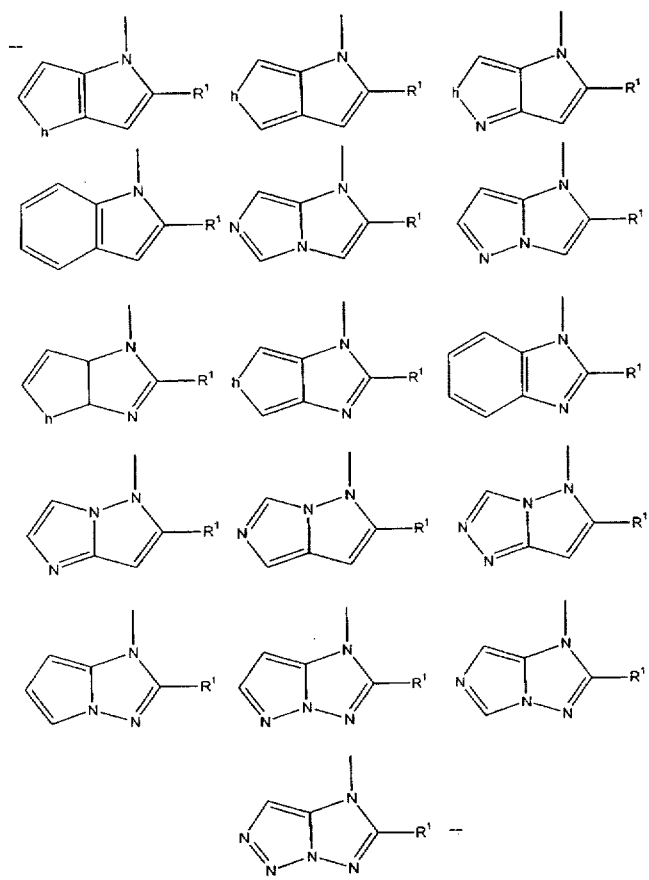

UNITED STATES PATENT AND TRADEMARK OFFICE
CERTIFICATE OF CORRECTION

PATENT NO. : 5,763,619
DATED : June 9, 1998
INVENTOR(S) : Yasushi SHIDA et al.

It is certified that error appears in the above-identified patent and that said Letters Patent is hereby corrected as shown below:

Column 16, line 65, delete:

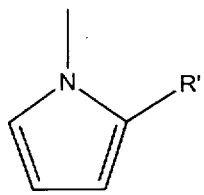 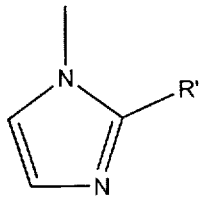 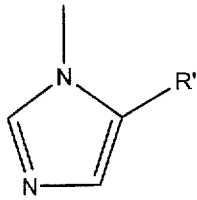

and insert therefor

-- 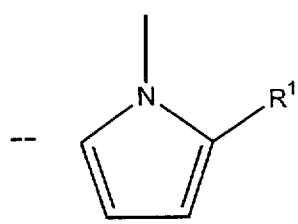 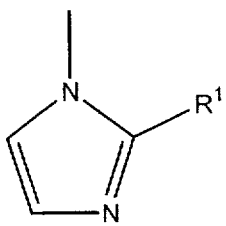 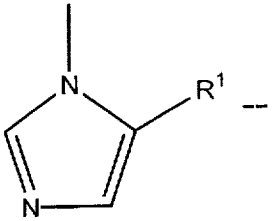 --

UNITED STATES PATENT AND TRADEMARK OFFICE
CERTIFICATE OF CORRECTION

PATENT NO. : 5,763,619
DATED : June 9, 1998
INVENTOR(S) : Yasushi SHIDA et al.

It is certified that error appears in the above-identified patent and that said Letters Patent is hereby corrected as shown below:

Column 17, lines 1-10, delete:

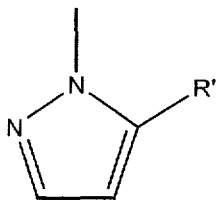 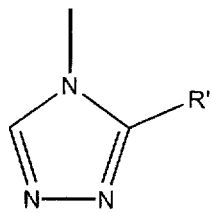 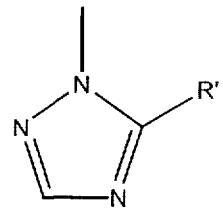

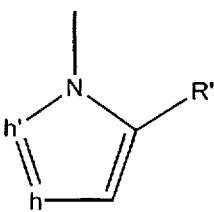 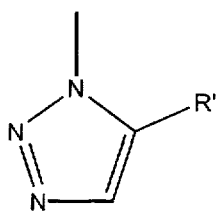 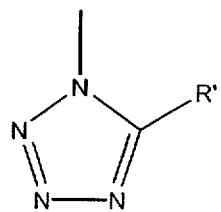

UNITED STATES PATENT AND TRADEMARK OFFICE
CERTIFICATE OF CORRECTION

PATENT NO. : 5,763,619
DATED : June 9, 1998
INVENTOR(S) : Yasushi SHIDA et al.

It is certified that error appears in the above-identified patent and that said Letters Patent is hereby corrected as shown below:

and insert therefor

-- 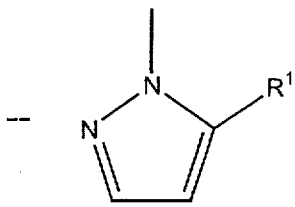 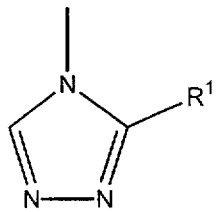 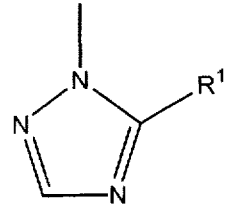

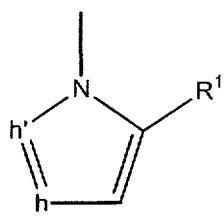 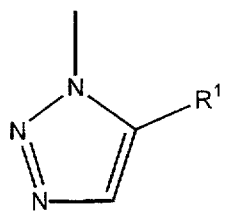 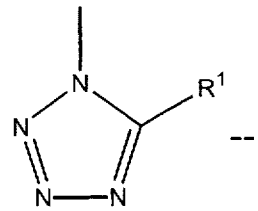 --

Signed and Sealed this

Twenty-third Day of March, 1999

Attest:

Q. TODD DICKINSON

*Attesting Officer*   Acting Commissioner of Patents and Trademarks